(12) United States Patent
Benner (10) Patent No.: US 7,563,887 B1
(45) Date of Patent: Jul. 21, 2009

(54) UNIVERSAL NUCLEOBASE ANALOGS

(76) Inventor: Steven Albert Benner, 1501 NW. 68th Ter., Gainesville, FL (US) 32605-4147

( * ) Notice: Subject to any disclaimer, the term of this patent is extended or adjusted under 35 U.S.C. 154(b) by 304 days.

(21) Appl. No.: 11/504,356

(22) Filed: Aug. 15, 2006

(51) Int. Cl.
*C07H 19/22* (2006.01)
(52) U.S. Cl. .................. 536/27.13; 536/22.1; 536/23.1; 536/27.1; 536/29.2
(58) Field of Classification Search ........................ None
See application file for complete search history.

(56) References Cited

OTHER PUBLICATIONS

McBride et al. J. Am. Chem. Soc. (1986), vol. 108, pp. 2040-2048.*

* cited by examiner

*Primary Examiner*—Patrick T Lewis (57) ABSTRACT

This invention relates to the field of nucleic acid chemistry, more specifically to the field of compositions and processes that can bind to nucleic acids, including compositions and processes that by doing so have use in the capture, detection and sequencing of nucleic acids, and most specifically to nucleoside analogs that incorporate nucleobase analogs that are able to bind to different natural nucleobases with nearly equal affinity, and therefore display a degree of ambiguity, or universality, in their binding pattern. Such nucleobase analogs, when incorporated into oligonucleotides, allow the oligonucleotides to bind with nearly equal affinity and/or melting temperature, to a complementary strand, template the synthesis of oligonucleotide from primers that have a distribution of sequences, and support the sequencing of oligonucleotides. Thus, these have use in human diagnostics, especially when polymorphisms are present in a population.

2 Claims, 9 Drawing Sheets

Figure 3 hydrogen bond pattern complementary to thymine/uracil hydrogen bond pattern complementary to guanine tautomerism Compound III hydrogen bond pattern complementary to cytosine hydrogen bond pattern complementary to adenine/aminoadenine

This presents a hydrogen bonding pattern like G to a complementary strand

⇅

This presents a hydrogen bonding pattern like A to a complementary strand

P

This presents a hydrogen bonding pattern like T to a complementary strand imine forms ⇅ tautomeric equilibrium amine forms This presents a hydrogen bonding pattern like C to a complementary strand

5-formyl-2'-deoxycytidine
[Rah01], prepared from
5=methyl-2'-deoxycytidine

Analog of Compound I. Note
how a methyl group and a fixed
positive charge are missing Compound I

Graboyes et al. (1968) *J. Med. Chem.* 11, 568-573.

and other isomers

UNIVERSAL NUCLEOBASE ANALOGS

FIELD

This invention relates to the field of nucleic acid chemistry, more specifically to the field of compositions and processes that can be used to detect nucleic acid analogs. Most specifically, this invention relates to nucleoside analogs that incorporate nucleobase analogs that are able to bind to different natural nucleobases, and therefore display a degree of ambiguity, or universality, in their binding pattern.

BACKGROUND

A universal pyrimidine-like nucleobase is defined as a nucleoside analog that forms a nucleobase pair with each of the two standard purine nucleobases (adenine and guanine) with equal (or nearly equal) facility, either as measured by the stability of the duplex, or by the preference for incorporation by DNA polymerases. For the purpose of practical application, "nearly equal" means that the difference is less than the difference normally seen with context dependence. Universal nucleobases have the potential for widespread application in research environments, where they could be very important in the design of universal primers and non-specific probes. Further, two large markets are emerging that would be enabled if pyrimidine-like universal nucleobases became available that met certain specifications with respect to promiscuous binding affinity to adenine and guanine.

The literature contains a large number of reviews of the "universal nucleobase" problem, various attempts in the past to solve it, and the utility of compositions that might solve it. This literature is incorporated herein by reference [Ber95] [Ber96] [Koo98] [Loa95a] [Loa95b] [Loa01] [Mar85] [Nic94] [Oht85].

The first of these commercial applications involves high throughput and highly parallel sequencing by synthesis, where the sequencing architecture involves ligation as the synthetic method. This approach is being developed in the laboratory of George Church at Harvard University, and at Agencourt Personal Genomics.

Another of these large-scale commercial applications involves the generation of simulants for the DNA of biohazard. The simulants would be distributed as part of a biohazard test assay kit for military and civilian preparedness. Here, one or more universal nucleobase analogs would prevent the simulant from itself being able to serve as this source of the biohazard DNA.

A universal nucleobase is defined as a nucleotide analogue that will pair with each of the four standard nucleobases with equal facility. Operationally, pairing facility is defined in two contexts. First, the ability of a universal nucleobase to pair may be defined in terms of the stability, often measured by melting temperature, of a duplex that contains one or more universal:standard pairs compared it to the stability of a reference duplex containing only standard:standard Watson-Crick nucleobase pairs.

Alternatively, the quality of a universal nucleobase may be defined by its ability to direct the incorporation of each of the four standard nucleotides with equal frequency in a reaction catalyzed by a DNA polymerase or reverse transcriptase. Conversely, a universal nucleobase will be added to a primer by DNA polymerases opposite standard nucleobases in a template with equal facility.

In the real world, perfect universal nucleobases (those that are perfectly promiscuous among the four standard nucleotides) are not known. For example, hypoxanthine has been used for many years as an approximation of a universal nucleobases. This has led to its application in degenerate primers, in probes for hybridization and in other contexts. Despite this use, it is clear that the compound is not indiscriminant in its nucleobase pairing properties [Oht85]. A wide range of melting temperatures is observed when hypoxanthine is placed opposite each of the four standard nucleobases [Oht85]. Further, primers containing multiple substitutions by inosine often give rise to sequence data that are difficult to analyze [Mar85].

A variety of other nucleobases have and proposed to mimic purines and/or pyrimidines with a greater sophistication. For example, azole carboxamides were proposed that could mimic both guanine and adenine in their hydrogen bonding patterns simply by rotating around the amide bond [Ber96]. As reviewed by Loakes [Lok01], for reasons that are not entirely clear, these compounds have been disappointing as nucleobases analogs, as one of the two conformational isomers appears to be preferred.

A third class of the universal nucleobases ideas has been based on the use of species that do not attempt to mimic alternative hydrogen bonding patterns displayed by the four standard nucleobases. Rather, these proposed nucleobase served simply to complete the hydrophobic stacking of the duplex. Bergstrom, for example, described 3-nitropyrrole as a candidate universal nucleobase [Ber95]. This analog was designed to maximize nucleobases stacking interactions. The nitro group was presumed to enhance stacking by polarizing the aromatic system. The same concept has been used to propose nitroindole as a universal nucleobase analog. 3-Nitropyrrole and 5-nitroindole are both sold by Glen Research as their protected DNA phosphoramidites.

3-Nitropyrrole does indeed pair with the four standard nucleobases. There is a range of melting temperatures observed, however, with nearly all pairs involving 3-nitropyrrole showing decreased stability [Ber95]. For example, in 15mers, the melting temperature drops by 11 to 14° C. (compared to 57° C. in the reference DNA duplex). The destabilization is still larger if multiple substitutions are made. These observations raise questions about how well the nitropyrrole stacks. Nitroindole appears to work better in this role. However, there is no question that DNA polymerases, including the error checking mechanisms that they contain, treat this species as foreign.

Much of the use of hydrophobic stacking nations lacking hydrogen bonds has been based on a general view that hydrogen bonding is not important to duplex recognition in DNA. It is difficult to understand why this view gained such currency in the modern biochemical community. Undoubtedly, the work by Eric Kool with fluorinated heterocycles [Koo98] that are accepted as substrates by some DNA polymerases has contributed to this view. It is clear, however, from the detailed studies by Geyer and Battersby in the Benner group [Gey03], studies that examined a very large number of nucleobase analogs, that hydrogen bonding and size complementarity contribute roughly equally to the ability of a nucleobase pair to stabilize a duplex. Non-complementary pyrimidine-pyrimidine pairs that can form three hydrogen bonds contribute to approximately the same to duplex stability as the size complementary nucleobase pairs that form only two interstrand hydrogen bonds (in natural DNA, the A:T base pair).

Further, it is clear that when polymerases are called upon to exercise their full discriminatory power against unnatural nucleobases analogs, they easily reject species that have a slight wobbles, lack unshared pairs of electrons in the minor groove, or have other structural features that are far more subtle than those introduced by the natural nucleobases

[Ben04]. Is has required over a decade in the Benner laboratory before combinations of polymerases and nucleobases analogs were obtained that enabled full of polymerase chain reaction amplification of DNA containing nucleobases that were not natural [Sis04] [Ben04].

Given the different sizes of purines and pyrimidines, many groups, instead of trying to develop a single nucleobases that binds equally to both purine and pyrimidine complements seek to generate purine-like universal nucleobases and pyrimidine-like universal nucleobases as separate entities. The first are designed to bind with equal affinities to T and C, while the second are designed to bind with equal affinities to A and G.

Figure 4:
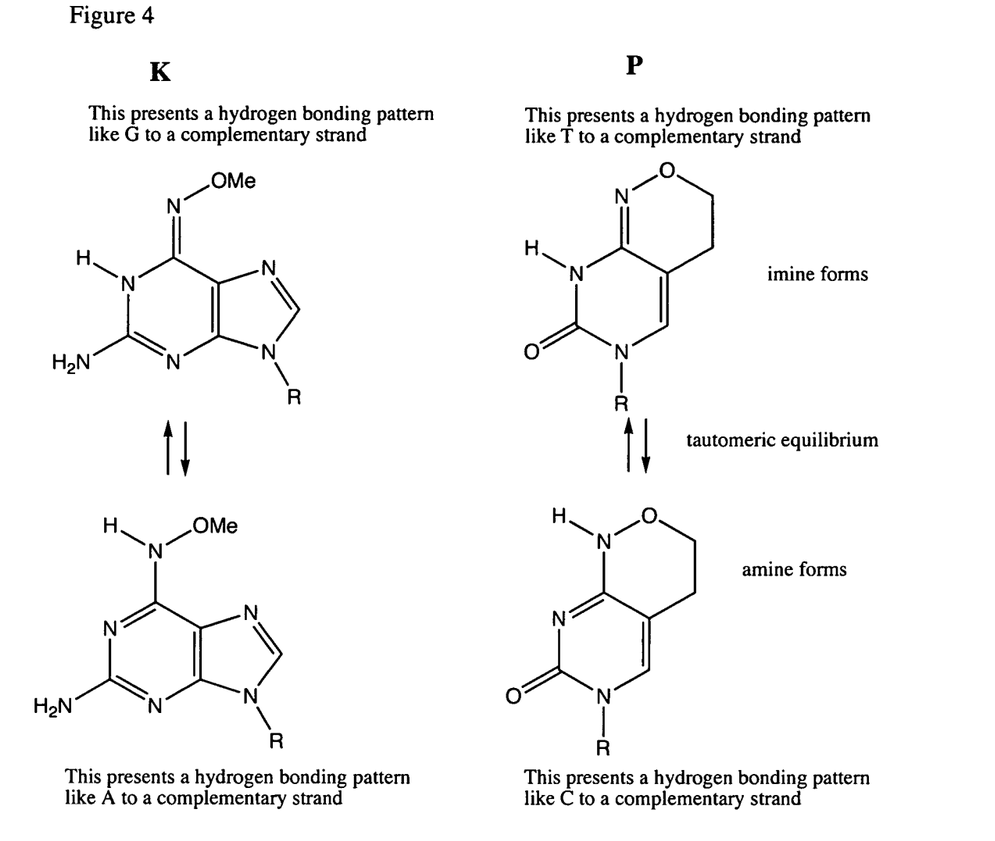
Figure 5:
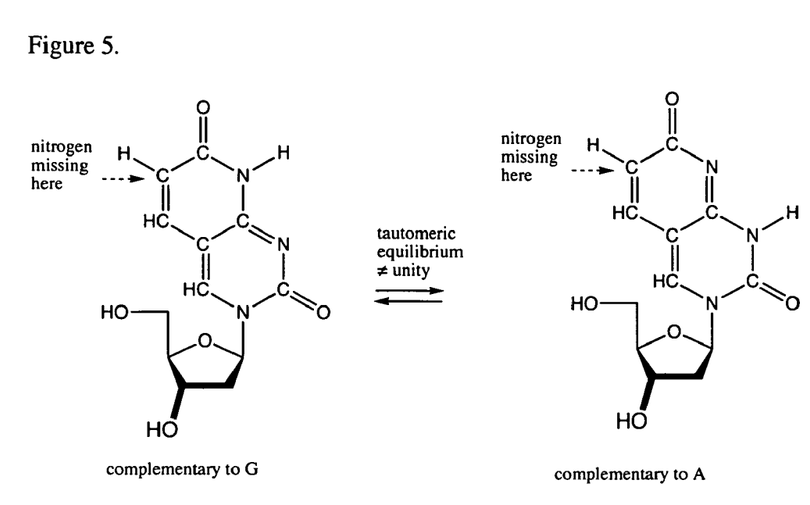

For example, Glen Research makes commercially available two compounds for this purpose. These are called K and P (FIG. 4). These attempt to capture some of the hydrogen bonding capabilities of natural purines and pyrimidines. For them to be effective universal purine-like and pyrimidine-like universal nucleobases, however the tautomeric equilibria displayed by the K and P compounds must have the equilibrium constants close to unity. In fact, these equilibrium constants are not close to unity, at least not to the degree that is necessary for these compounds to meet the specifications required for sequencing by ligation and simulants.

Recent efforts in the development of high throughput sequencing methods have illustrated the need for universal nucleobases that meet higher standards. Both the Church laboratory at the Harvard Medical School and Agencourt are attempting to develop highly parallel sequencing by synthesis strategies that use ligation as the key step. In this strategy have, rather than add a single nucleotide to a growing template in the 5' to 3' direction, they ligate a compound from a library of short segment to the 5' end of the DNA. One typical sequencing-by-ligation architecture ligates a 10mer. Here, the first nucleobase is A, T, G, or C, which queries the site in the sequence that is to be determined. Following the query nucleotide is a segment of nine nucleotides that forms a paired duplex with the target sequence. Some of the sites in this segment containing all four nucleotides, creating large libraries. At other sites, attempts are being made to introduce universal nucleobase so as to diminish the size of the library.

Special attention is paid to the sequence of five nucleotides immediately following the query nucleotide. Typical DNA ligases require five paired nucleotides in the duplex that occupies the binding site of the enzyme.

The simplest approach to create this outcome would be simply to make a library where each of the four standard nucleobases (ATGC) is present at each site to the extent of 25%. To do so for the five paired nucleotides in the binding site would require a library of 1024 different sequences to follow the query nucleotide. This library is already large, and leads to slow hybridization and significant mismatch.

It would be desirable to have improved universal nucleobases that would be placed in this region. For each pyrimidine-like universal nucleobase added, the degeneracy of the library could be decreased by factor of two.

Various groups had hoped to use inosine as a universal nucleobase been the region of the five nuclear base pairs. This would obviate the need to synthesize a multiple libraries containing large numbers of compounds. This universal base has not proved to be adequate however. The universal nucleobases to be developed in this research under the phase one grant that is sought in this application should be able to serve in need roles sufficient to meet the specifications sought in sequencing-by-ligation strategies. The Church laboratory, Agencourt, and other organizations attempting to implement sequencing-by-ligation would be potential customers for Firebird Biomolecular.

Another new application for universal nucleobases could be opened given a high quality universal nucleobase. This application concerns simulants to be used in kits that test for the presence of biohazards by seeking the nucleic acid of the biohazard in the environment being assayed. Field-ready kits to detect biological hazards need to include a positive standard.

Substance that response to the assay in the kit just as the natural biohazard does, and therefore allows the user in the field to be certain that the kit was functioning correctly.

The DNA from the biohazard itself, of course, could serve as the authentic standard for a kit. Thus, it is possible to include smallpox DNA as a positive standard in a kit designed to detect smallpox. If the DNA is only a small fragment of the total smallpox gene, it is conceivable that the presence of actual smallpox DNA might present little actual risk, and could actually be distributed as part of the kit. It would, of course, present a perceived risk.

Further, if the authentic standard is a piece of DNA that represents a larger fraction of the smallpox genome, the risk associated with the dispersion of large amounts of actual pathogen DNA will become real and unacceptable.

These considerations lead to the demand for simulants. A useful simulant is a DNA molecule that will blind to any probe that is presented to detect the biohazard nucleic acid. For essays that involve the template directed polymerization of species from the biohazard, the simulant must also serve as a template for a DNA polymerase. At the same time, it is desirable to have structures within the simulant that make it impossible to generate the native biohazard DNA by a template directed polymerization of the simulant itself.

The introduction of a pyrimidine-like universal nucleobase at points within the simulant offers one strategy to meet these goals. Especially if the simulant contains a C-glycosides (as in Compound I, FIG. 1), it will not be copied by mammalian DNA polymerases, something that has been shown by the Benner Research Group a decade ago [Hor95]. Further, the simulant containing the universal basis at strategic sites will be able to bind to any probe that is delivered, with the loss of specificity against probes that are not present being the only consequence. Further, given n universal nucleobases the templates, an attempt to transcribe would generate a defective sequence, where the likelihood of the correct biohazard sequence declining as a function of 2'. While this does not absolutely preclude the generation of biohazard DNA from the simulant in the test kit, it greatly diminishes the likelihood that it can be.

BRIEF DESCRIPTION OF THE DRAWINGS

FIG. 1. A C-glycoside, Compound I, that has a tautomeric equilibrium that permits it to present hydrogen bonding patterns that are complementary to either guanine or cytosine in a complementary strand.

FIG. 2. An N-glycoside, Compound II, that has a resonance form that permits it to present hydrogen bonding patterns that are complementary to either guanine or cytosine in a complementary strand. Note that the methyl group on the heterocycle can also be a proton.

FIG. 3. A heterocycle that serves as a universal nucleobase analog with the ability to bond to A, T, G, or C in a complementary strand.

FIG. 4. Nucleoside analogs in the art that are sold as universal nucleobases.

FIG. 5. Analog of Compound II reported by Inouye et al. in 1985-[Ino85]. Note the missing nitrogen, which makes the equilibrium constant between the two tautomeric forms not equal to unity. Nevertheless, this can also serve as a universal nucleobase, and its incorporation into oligonucleotides for this purpose is part of the instant invention.

DESCRIPTION OF THE INVENTION

Figure 1:
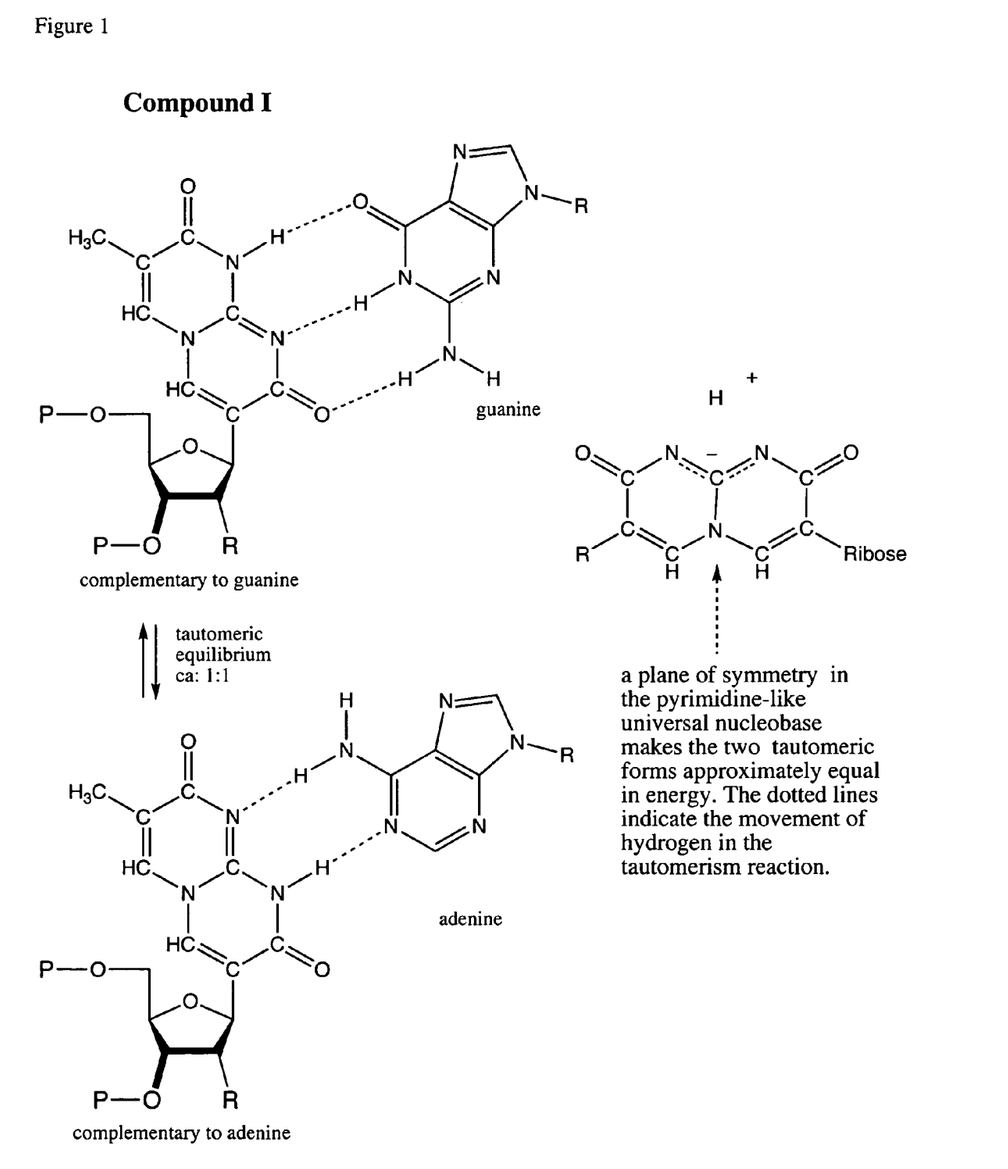
Figure 2:
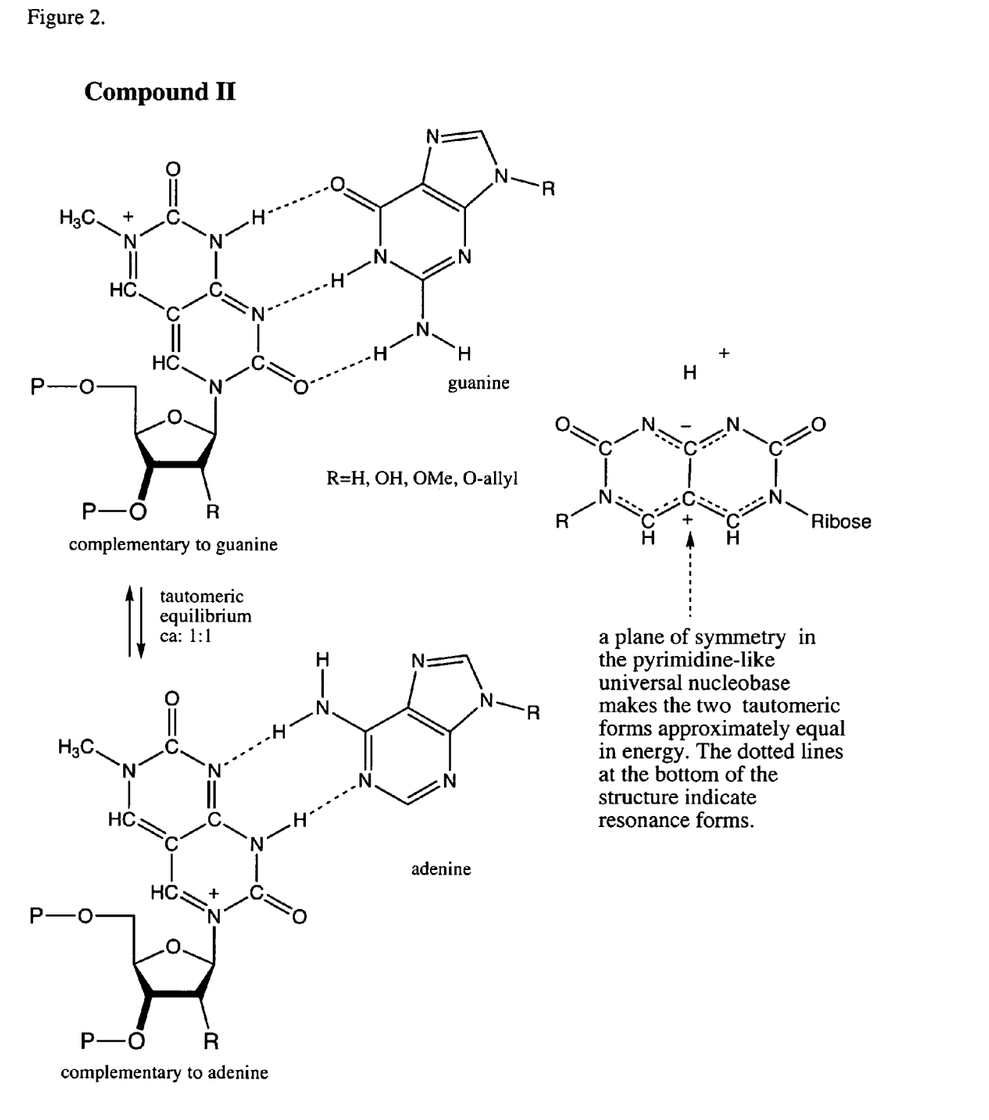
Figure 3:
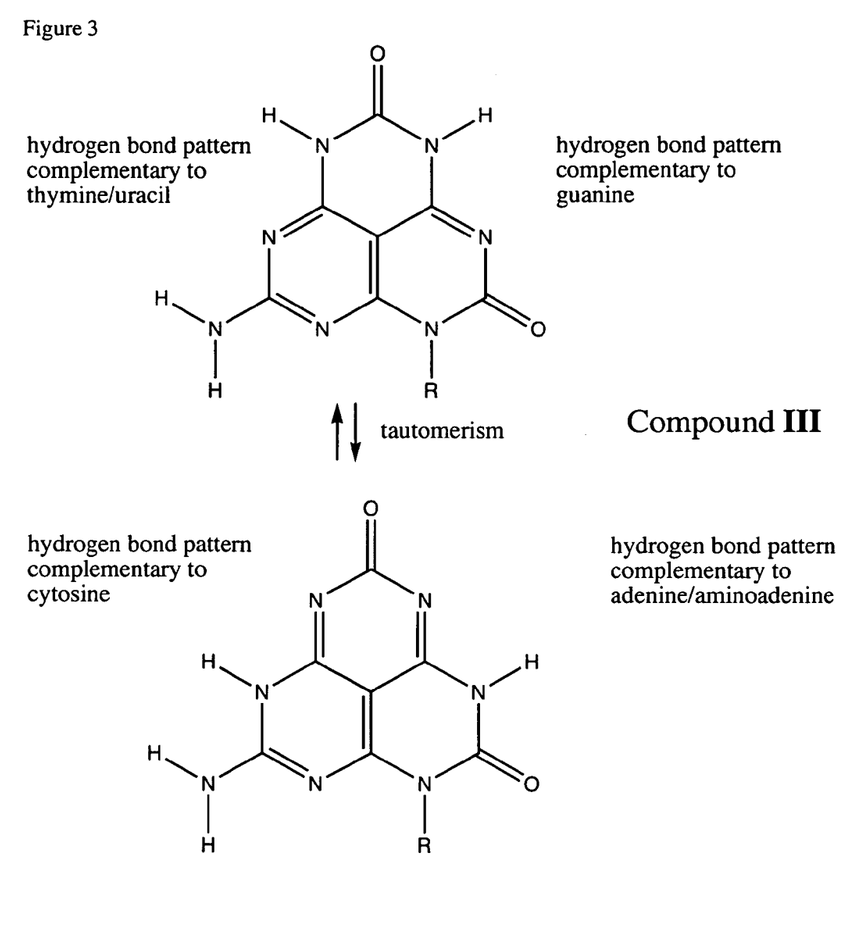

Two structures, shown in FIG. 1 and FIG. 2, and named Compound I and Compound II, represent pyrimidine-like universal nucleobases that are the objects of the instant invention. A third structure, shown in FIG. 3 and named Compound III, is able to act both like a pyrimidine and like a purine, and is a third object of the instant invention. This invention covers these nucleobases placed on a ribose or ribose analog (such as 2'-O methyl, 2'-O allyl, or other modified ribose ring, including deoxyribose), LNA or other ribose analog having the conformational flexibility constraints, PNA or other analog of DNA with the charges missing, and glycerol DNA, glyoxal DNA, or other analogs of nucleic acids where an open ring, abbreviated, or other sugar analog is used. The nucleobases are also covered in the instant invention if they are appended to a triphosphate of a sugar, in a form suitable for incorporation into a DNA or RNA molecule by a polymerase or reverse transcriptase. Also covered are oligonucleotides containing the nucleobases in DNA analogs that are branched, dendrimeric, cyclic, derivatized. (e.g., with a fluorescent tag) and/or immobilized.

The strategy disclosed in this specification for inventing a pyrimidine-like universal nucleobase was to ensure that the nucleobase analog can present a full hydrogen bonding pattern to a standard purine on the complementary strand, where two tautomeric forms present the two different hydrogen bonding patterns. In the design of the molecule, the goal is to have the two tautomeric forms have as nearly equal energies as possible, so that the equilibrium constant between the two is as near to unity as possible.

This requires the construction of molecules that have high degrees of symmetry. While perfect symmetry is not possible, as there is only one ribose ring, if the ribose is assumed to contribute to electronic distribution as a standard alkyl group, an alkyl group at the appropriately symmetric position create the appropriate symmetry.

The design of pyrimidine-like universal nucleobases also takes advantage of the extensive studies that show that most DNA polymerases are largely insensitive to the placement of bulky side chains in the major groove. This has been exploited for over two decades in DNA sequencing and DNA labeling. The ability of ligases to accept large substituents in the major group is less well studied, but this region also appears to tolerate substitution at nucleotides at positions other than the nucleotide that is directly participating in the ligation reaction.

Several features of these compounds should be noted. First, compound one is a C-glycoside. This means that the heterocyclic nucleobase is joined to the sugar by a carbon-carbon bonds, rather than the carbon-nitrogen bond that joins the nucleobase to the sugar in a standard nucleotide. Preliminary work at the Foundation has shown that some polymerases, such as Therminator, will accept a string of 12 C-glycosides in row. Obviously, an applications here, the level of C-glycoside incorporation will be lower.

Compound II contains a positive charge in the nucleobase period through resonance, this positive charge is distributed up and down the two fused ring systems. Geyer et al. [Gey03] showed that introduction of a positive charge into a nucleobase stabilized the duplex modesty. We do not expect, of course, that multiple stacked cationic nucleobases would be desirable. The corresponding species without the methyl group on the nitrogen does not have a positive charge. It lacks, however, some of the symmetry that ensures that the tautomeric equilibrium constant is close to unity.

FIGS. 1 and 2 shows the rationales by which compounds I and compounds II were designed. Both structures display high levels of symmetry and electronic distribution that is necessary to ensure that two tautomeric forms are close in energy. Inspection of the structure shows that in each case, one of the tautomeric forms presents the hydrogen bond acceptor-donor-acceptor pattern characteristic of thymidine, while the other presents the hydrogen bonding pattern donor-acceptor-acceptor characteristic of cytidine. Because of the symmetry, it is likely that a DNA incorporating compound one or compound to at a site will bind with nearly equal affinity to adenosine and guanosine in the complementary nucleotide at the paired site.

As the modification involves only the introduction of extra material into the major groove, we expect Compound I and Compound II in a template to be accepted by most polymerases. We also expect that these compounds will be accepted by ligase in the five paired nucleotide that bind in the active site. It remains an open question, to be determined in phase 1 work, whether either compound can be excepted by a ligase at the site of ligation.

It is interesting to note that two decades ago, Inoue et al. prepared a pyridopyrimidine structure that is similar to the structure of the Compound II [Ino85] (specifically, 3-beta-D-2'-deoxyribofuranosyl-2,7-dioxopyrido[2,3-d]pyrimidine and its ribo counterpart). This compound lack the second nitrogen, and therefore the full symmetry of Compound II. Curiously, although these authors report that the compound forms hydrogen bonds with G (more strongly) and A (more weakly), they evidently did not recognize the tautomeric ambiguity of the species, nor the asymmetry in the compound, nor that the differences in binding affinity might arise because adenine presents only two hydrogen bonding opportunities, while guanine presents three. Instead, they propose that the binding to A is via a wobble structure.

The same analysis is involved in analysis of III, with the additional observation that it can exist in either the syn conformer around the glycosidic bond, or the anti conformer. In the syn conformer, tautomeric forms exist that are complementary, in a hydrogen bonding sense, to A and G. In the anti conformer, tautomeric forms exist that are complementary, in a hydrogen bonding sense, to T and C.

Further, we disclose that the sugar that carries the nucleobase analog heterocycle can be (preferably) 2'-deoxyribose. More stable binding can be had, however, if the sugar is ribose, or one of its hydrolytically stable variants, including 2'O-methyl ribose. In addition, we disclose that the glycerol sugar analogs of Zhang et al. [Zha05] are suitable to support these sugars. Further, because the pyrimidine analogs lack hydrogen bonding opportunities in the major groove, they can be supported on a PNA backbone. This is not the case, however, for structure III.

EXAMPLES

Example 1

A pyrimidine-Like Universal Nucleobase that is an N-Glycoside

Figure 6:
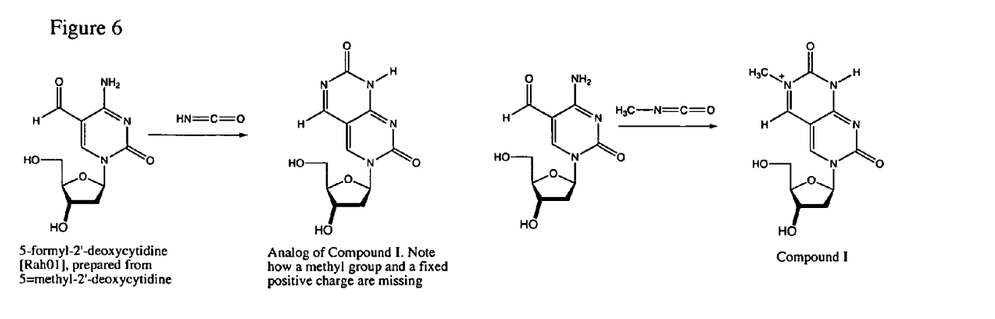
FIG. 6. Synthetic route to Compound II starting from 5-formylcytidine [Abd01].

The starting procedure for the compound represented by structure II is 5-formyl-2'-deoxycytidine (FIG. 6). This is prepared using the procedure presented by Abdel Rahman in 2001 [Abd01]. Other sources of this compound are found in [[Bie96] [Ita91] [Ita94]] [LaF98] [LAF00] [Mur99], and it is also known as a natural product [Kas98][Kaw94][Mor94], [Tom97] and is known as the 2'-OMe riboside as well [Pai96] [ ] [ ]. Commercially available 5-methyl-2'-deoxycytidine (30 mmol) is dissolved in dry pyridine (100 mL), and the solution is cooled on ice. To this is added tbutyldimethylsilyl chloride (33 mmol). After incubation at 0° C. for 5 hours, the reaction is quenched by the evaporation of the solvents under high vacuum at temperatures less than 40° C. The residue is then suspended in a mixture of water and ether, the ether layer is recovered, and the layer is dried and evaporated to give the 5'pmethyl-2'-deoxycytidine as its 5'-tbutyldimethylsilyl ether;

The product from the step above was treated with $Na_2S_2O_8$ to give a mixture of 5-(hydroxymethyl)- and 5-formyl-2'-deoxycytidine as products. These are separated by chromatography (silica, EtOAc). The second product is the precursor of the The hydroxymethyl group of the first product (4 mmol) is oxidized to a formyl group by treatment with ceric(IV) ammonium nitrate (CAN, 1 M) at 60° C. for 1 h. This product is also purified by chromatography (silica, EtOAc).

The 5'-formyl-2'-deoxycytidine (5 mmol), after coevaporation with dry pyridine, is converted to the 3'-5'-bis(trimethylsilyl ether by reaction with bistrimethylsilyl acetamide (2.2 equiv) at 0° C. in dry pyridine. The reaction mixture is then directly treated with methyl isocyanate, (1.05 equiv, 0° C., 2 hours) to yield II. The product is purified by column chromatography (silica, EtOAc).

This nucleoside analog is used as the starting point for the preparation of an activated phosphoramidite for oligonucleotides analog synthesis. The heterocycle itself need not be protected, as it does not carry any exocyclic amino groups, but the 5'-OH group must be protected, as always. Thus, the nucleoside analog (17.4 mmol) is dissolved in dry pyridine (250 mL). To the solution is added 4',4"-dimethoxytrityl chloride (1.2 equiv). The reaction mixture is stirred at room temperature for 24 hours. The reaction is then quenched by the addition of water (6 mL). The solution is concentrated under vacuum, and an aqueous solution of $NaHCO_3$ (150 mL) is added. The mixture is extracted with EtOAc, dried ($Na_2SO_4$), the solvents evaporated under reduced pressure, and the product isolated by column chromatography (chloroform/acetone 9:1, then 9:2).

The product from above (0.12 mmol) is dissolved in $CH_3CN$ (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure [McBride, L. J., Kierzek, R., Beaucage, S. L. & Caruthers, M. H. (1986) *J. Am. Chem. Soc.* 108, 2040-2048]. The progress of the reaction is monitored by TLC ($SiO_2$ eluted with $EtOAc:CH_2Cl_2$:triethylamine 45:45: 10). An additional portion (0.02 mL) of bis-(N,N-diisopropylamino)-3-cyanoethyloxyphosphine is then added, and stirring continued for an additional hour. Water (2 drops) is added, the mixture stirred for 15 min, the mixture diluted with $CH_2Cl_2$ (30 mL), and the organic layer washed with aqueous $Na_2CO_3$ (2%) and dried ($Na_2SO_4$). The phosphoramidite (120.3 mg, 93%) is isolated by chromatography ($SiO_2$, $EtOAc:CH_2Cl_2$:triethylamine 45:45:10 as eluant).

Alternatively, the protected species is be converted to its triphosphate via the procedure of Ludwig and Eckstein [Lud89]. In this procedure, the first intermediate is the 3'-protected acetate. The product is then detritylated to yield the 5'-deprotected-3'-acetate as the intermediate that is then used to generate a triphosphate.

Example 2

A Pyrimidine-Like Universal Nucleobase that is a C-Glycoside

Figure 7:
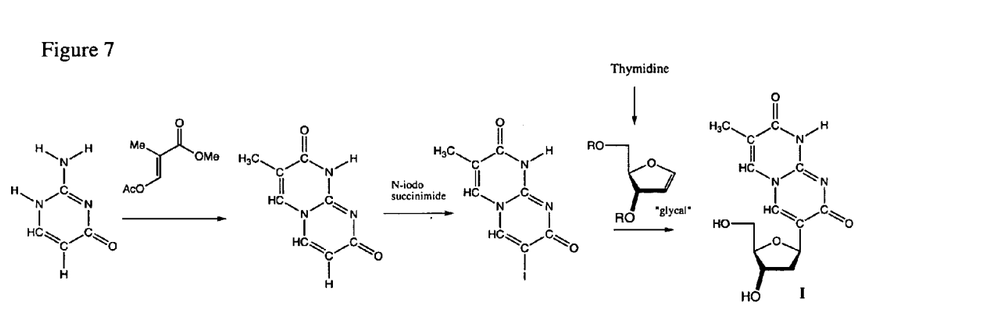
FIG. 7. Synthetic route to Compound I starting from isocytidine using chemistry analogous to that described by [Sto91]

The heterocycle found in Compound I is known from the work of Stoss et al. [Stoss91]. It is also was prepared by the condensation of guanidine and 3-methoxyacrylate esters [Tan02]. Synthesis of I from that heterocycle involves coupling of the iodinated heterocycle to the known glycal prepared from thymidine (FIG. 7).

Figure 8:
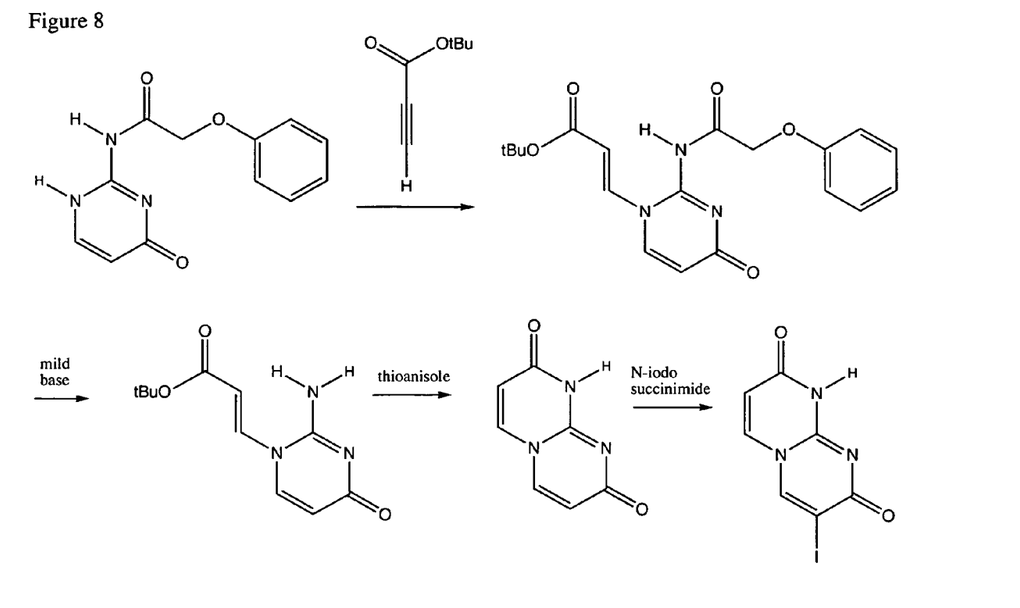
FIG. 8. Alternative synthetic route to Compound I starting from isocytidine.

An alternative approach is available to prepare the nucleoside carrying this heterocycle (FIG. 8). Here, the commercially available 2-amino-4(1H)-pyrimidinone (isocytidine) is phenoxyacetylated and treated with the t-butyl ester of propargylic acid. This gives a product with the double bond having primarily the trans configuration. The phenoxyacetyl group is removed to generate the free amine. This closes spontaneously when the double bond is in the cis form, upon Michael addition by thioanisol to give the beta thioether (FIG. 8).

The heterocycle (14 mmol) is rendered anhydrous by coevaporation with DMF under high vacuum. The dry material is then dissolved in DMF (50 mL). N-Iodosuccinimide (4.73 g; 21 mmol) is added and the resulting solution is stirred at room temperature in the dark. After 4 days, the solution is slowly added to vigorously stirred water (2 L) and the resulting suspension is stirred overnight. The solid iodinated heterocycle is recovered by filtration and dried in a vacuum over $P_2O_5$ gives the product as a yellow solid.

The iodinated heterocycle is then coupled to 3-tertbutyl-diphenylsilyloxy-2-hydroxymethyl-2,3-dihydrofuran, which is well known in the literature [Hut03] [Ire80] [Lar94] [Wal96] [Cam97], and referred to here as simply the "glycal". The Heck coupling is done following literature procedures, using palladium acetate with triphenylarsine as the catalyst system, and anhydrous dimethylformamide (DMF) as the solvent. The coupling to the glycal and subsequent deprotection and reduction have been reported previously by several groups [Farr, R. N. Outten, R. A. Cheng, J. C.-Y. Daves, Jr., G. D. (1990) Organometallics 9, 3151][Zhang, H.-C. Daves, Jr., G. D. (1992) *J. Org. Chem.* 57, 4690][Zhang, H.-C. Daves, Jr., G. D. (1993) *Organometallics* 12, 1499][Hsieh, H.-P. McLaughlin, L. W. (1995) *J. Org. Chem.*, 60, 5356][Chen, D. L. McLaughlin, L. W. (2000) *J. Org. Chem.*, 65, 7468.] [Searls, T. Chen, D. L. Lan, T. McLaughlin, L. W. (2000) *Biochemistry*, 39, 4375.][Lan, T.; McLaughlin, L. W. (2001) *Bioorg. Chem.* 29, 198] [Coleman, R. S., Madaras, M. L. (1998) *J. Org. Chem.* 63, 5700]. Triethylamine is often used instead of tributylamine as the base, since it is easier to remove during purification.

Thus, a suspension of palladium acetate (7 mg, 0.031 mmol) and triphenyl arsine (19 mg, 0.061 mmol) in DMF (2 mL) is stirred at room temperature for 30 min, to give a yellow suspension. A solution of the iodinated heterocycle (0.204 mmol) and the 3-TBDPS-5-unprotected glycal (109 mg, 0.307 mmol) is prepared in DMF (3 mL) and dried overnight over molecular sieves (4 Å). This solution is added to the yellow suspension, followed immediately by addition of triethylamine (0.06 mL, 0.408 mmol). The suspension is stirred at 55° C. for 2 days. The solvent is removed under high vacuum. The residue is suspended in $CH_2Cl_2$ (60 mL), the insoluble material removed by filtration and the organic solution evaporated. Column chromatography on silica (hexane:

EtOAc=2:1 to 1:1.5 as eluant gives the coupled product, with some of the TBDPS removed. Therefore, the mixture is reduced rapidly (net step).

Sodium triacetoxyborohydride (0.549 g, 2.475 mmol) is added in one lot to a solution of the product of the previous step (1.65 mmol) in acetonitrile (8 mL) and acetic acid (4 mL) under an Ar atmosphere. TLC (ethyl acetate) indicated that there is no starting material after 12 min. The reaction is quenched by the addition of acetone, and the reaction mixture concentrated under reduced pressure. The resulting pale yellow gum is dissolved in methanol, adsorbed onto silica, and purified by flash chromatography (ethyl acetate) to give the desired material as a white solid.

This nucleoside analog is used as the starting point for the preparation of an activated phosphoramidite for oligonucleotides analog synthesis. The heterocycle itself need not be protected, but the 5'-OH group must be protected, as always. Thus, the nucleoside analog (8.7 mmol) is dissolved in dry pyridine (150 mL). To the solution is added 4',4"-dimethoxytrityl chloride (1.2 equiv). The reaction mixture is stirred at room temperature for 24 hours. The reaction is then quenched by the addition of water (3 mL). The solution is concentrated under vacuum, and an aqueous solution of $NaHCO_3$ (80 ml) is added. The mixture is extracted with EtOAc, dried ($Na_2SO_4$), the solvents evaporated under reduced pressure, and the product isolated by column chromatography (chloroform/acetone 9:1, then 9:2).

The product from above (0.12 mmol) is dissolved in $CH_3CN$ (2.0 mL). The solution is then treated with bis-(N,N-diisopropylamino)-3-cyanoethyloxyphosphine (Aldrich, 1.2 equiv.), and diisopropylammonium tetrazolide (0.06 mmol), following a literature procedure [McBride, L. J., Kierzek, R., Beaucage, S. L. & Caruthers, M. H. (1986) *J. Am. Chem. Soc.* 108, 2040-2048]. The progress of the reaction is monitored by TLC ($SiO_2$ eluted with $EtOAc:CH_2Cl_2$:triethylamine 45:45:10). An additional portion (0.02 mL) of bis-(N,N-diisopropylamino)-3-cyanoethyloxyphosphine is then added, and stirring continued for an additional hour. Water (2 drops) is added, the mixture stirred for 15 min, the mixture diluted with $CH_2Cl_2$ (30 mL), and the organic layer washed with aqueous $Na_2CO_3$ (2%) and dried ($Na_2SO_4$). The phosphoramidite (120.3 mg, 93%) is isolated by chromatography ($SiO_2$, $EtOAc:CH_2Cl_2$:triethylamine 45:45:10 as eluant).

Alternatively, the protected species is be converted to its triphosphate via the procedure of Ludwig and Eckstein [Lud89]. In this procedure, the first intermediate is the 3'-protected acetate. The product is then detritylated to yield the 5'-deprotected-3'-acetate as the intermediate that is then used to generate a triphosphate.

Example 3

Figure 9:
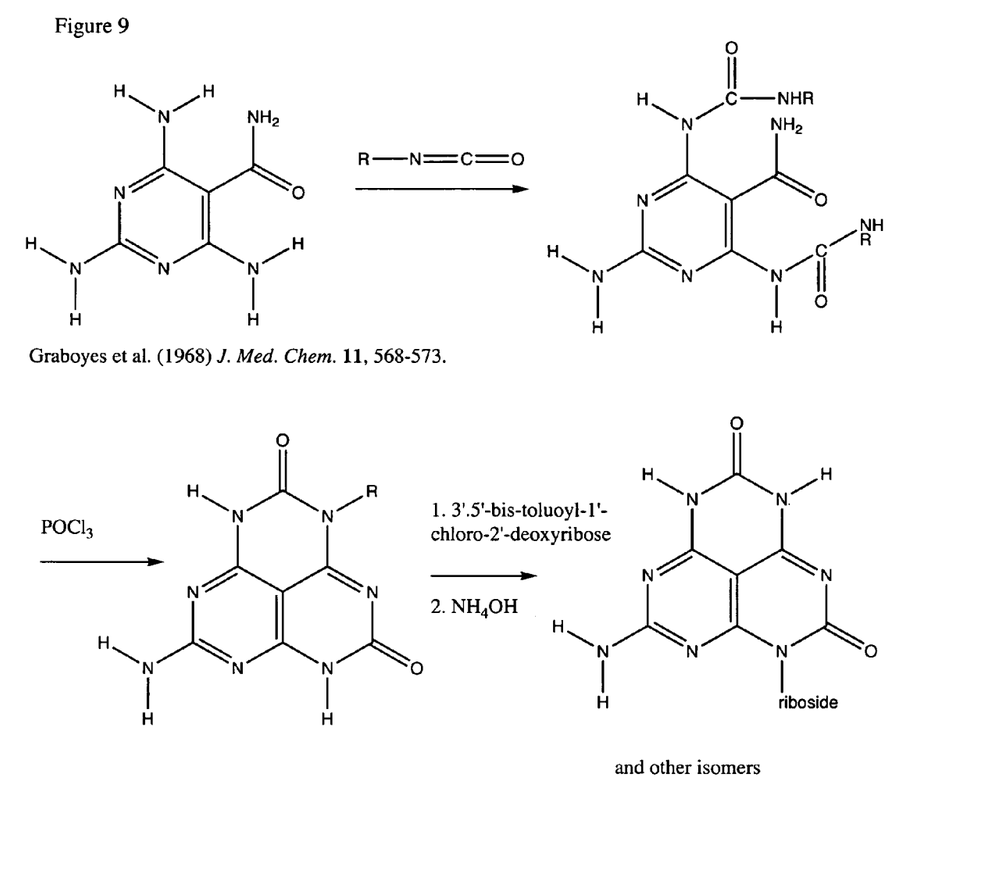
FIG. 9. Route for the synthesis of Compound III.

A Compound that Serves as Both a Universal Purine and Pyrimidine Nucleobase A route for the synthesis of III is shown in FIG. 9 from a structure that is reported in the literature [Graboyes et al. (1968) *J. Med. Chem.* 11, 568-573]. This compound (2.8 mmols) is covaporated with pyridine three times to ensure that it is dry. The compound is then dissolved in dry pyridine (10 mL), and the solution is treated with $CH_3NCO$ (2.1 equiv., R=Me). This material is then suspended in phosphorous oxychloride (10 mL, 0° C.), and the mixture is allowed to warm to room temperature, and then under Ar to 80° C. to give the heterocycle.

This heterocycle is then converted to a riboside, a riboside derivative, or a 2'-deoxyriboside using any standard electrophile. For the case in FIG. 9, a slurry of the heterocycle (17.8 mmol), $K_2CO_3$ (58 mmol), and tris[2-(2-methoxyethoxy)ethyl]amine (0.20 mL, 0.42 mmol) in anhydrous acetonitrile (1000 mL) is stirred at room temperature for 1 h. At this time, bis-tolyl protected 1-chloro-2'-deoxyribose (Berry & Associates, 9 g, 23.2 mmol) is added. The stirring is continued for two hours. After the coupling is complete, the solids are removed by filtration, the filtrate is recovered, and the solvents are removed under vacuum. The product present in the residue is purified by column chromatography on silica gel using 1-2% $Me_2CO/CH_2Cl_2$ as eluant to yield the title compound as a white foam, along with a mixture of other isomers.

REFERENCES

Ireland, R. E., Thaisrivongs, S., Vanier, N., Wilcox, C. S. (1980) *J. Org. Chem.* 45, 48

Larsen, E., Jorgensen, P. T., Sofan, M. A, Pedersen, E. B. (1994) *Synthesis*, 1037

Walker II, J. A., Chen, J. J., Wise, D. S., Townsend, L. B. (1996) *J. Org. Chem.* 61, 2219

Cameron, M. A.; Cush, S. B.; Hammer, R. P. (1997) *J. Org. Chem.* 62, 9065]

Abdel Rahman, A. A.-H., Wada, T., Saigo, K. (2001) Facile methods for the synthesis of 5-formylcytidine. *Tetrahedron Letters* 42, 1061-1063.

Bergstrom, D. E., Zhang, P., Toma, P. H. Andrews, P.C., Nichols, R. (1995) Synthesis structure and deoxyribonucleic acid sequencing with universal base: 1-(2'-Deoxy-B-D-ribofuranosyl)-3-nitropyrole. *J. Am. Chem. Soc.* 117, 1201-1209.

Bergstrom, D. E., Zhang, P. M. Johnson, W. T. (1996) Design and synthesis of hetrocyclic carboxamide as natural nucleic-acid base mimic. *Nucleos. Nucleot.* 15, 59-68.

Bienvenu, C., Wagner, J. R., Cadet, J. (1996) Photosensitized oxidation of 5-methyl-2'-deoxycytidine by 2-methyl-1,4-naphthoquinone: Characterization of 5-(hydroperoxymethyl)-2'-deoxycytidine and stable methyl group oxidation products. *J. Am. Chem. Soc.* 118, 11406-11411.

Geyer, C. R., Battersby, T. R., Benner, S. A. (2003) Nucleobase pairing in expanded Watson-Crick like genetic information systems. *Structure* 11, 1485-1498

Horlacher, J., Hottiger, M., Podust, V. N., Hübscher, U., Benner, S. A. (1995) Expanding the genetic alphabet: Recognition by viral and cellular DNA polymerases of nucleosides bearing bases with non-standard hydrogen bonding patterns. *Proc. Natl. Acad. Sci.* 92, 6329-6333

Hutter, D., Benner, S. A. (2003) Expanding the genetic alphabet. Non-epimerizing nucleoside with the pyDDA hydrogen bonding pattern. *J. Org. Chem.* 68, 9839-9842

Inoue, H., Imura, A., and Ohtsuka, E., (1985) Synthesis and hybridization of dodecadeoxyribonucleotides containing a fluorescent pyridopyrimidine deoxynucleoside. *Nucleic Acids Res.* 13, 7119-7128.

Itahara, T. (1991) Oxidation of cytosine and 5-methylcytosine nucleosides and 5-methyl-2'-deoxycytidine 5'-monophosphate with peroxosulfate ions. *Chemistry Lett.* (9), 1591-1594.

Itahara, T., Yoshitake, T., Koga, S., Nishino, A. (1994) Oxidation of nucleic acid related compounds by the peroxodisulfate ion. *Bull. Chem. Soc. Japan* 67, 2257-64.

Kashiwai, T., Takemoto, C., Ohtsuki, T., Kawai, G., Watanabe, K. (1998). NMR study on non-universal codon recognition by mitochondrial tRNA possessing a modified nucleoside 5-formylcytidine. *Nucleic Acids Symp. Series* 39, 155-156

Kawai, G., Yokogawa, T., Nishikawa, K., Ueda, T., Hashizume, T., McCloskey, J. A., Yokoyama, S.,; Watanabe, K. (1994). Conformational properties of a novel modified nucleoside, 5-formylcytidine, found at the first position of the anticodon of bovine mitochondrial tRNAMet. *Nucleos. Nucleot.* 13, 1189-99.

Kool, E. T. (1998) Replication of non-hydrogen bonded bases by DNA polymerases: a mechanism for steric matching. *Biopolymers* 48, 3-17.

La Francois, C. J., Fujimoto, J., Sowers, L. C. (1998) Synthesis and characterization of isotopically enriched pyrimidine deoxynucleoside oxidation damage products. *Chem. Res. Toxicol.* 11, 75-83.

La Francois, C. J., Jang, Y. H., Cagin, T., Goddard, W. A., III, Sowers, L. C. (2000) Conformation and proton configuration of pyrimidine deoxynucleoside oxidation damage products in water. *Chem. Res. Toxicol.* 13, 462-470.

Loakes, D. (2001) The applications of universal DNA base analogs. *Nucl. Acids Res.* 29, 2437-2447.

Loakes, D., Brown, D. M., Linde, S., Hill, F. (1995) The synthesis of bicyclic N-4-amino-2'-deoxycytidine derivatives. *Nucl. Acids Res.* 13, 2361-2366.

Loakes, D., Hill, F., Linde, S., Brown, D. M. (1995) nitroindoles as universal bases *Nucleos. Nucleot.* 14, 1001-1003.

Ludwig, J., Eckstein, F. (1989) Rapid and efficient synthesis of nucleoside 5'-o-(1-thiotriphosphates), 5'-triphosphates and 2',3'-cyclophosphorothioates using 2-chloro-4H-1,3,2-benzodioxaphosphorin-4-one. *J. Org. Chem.* 54, 631-635

Martin, F. H., Castro, M M., Aboul-ela, F, Tinoco, I. (1985) Base-pairing involving deoxyinosine-implication for probe design. *Nucl. Acids Res.* 13, 8927-8938.

Moriya, J., Yokogawa, T., Wakita, K., Ueda, T., Nishikawa, K., Crain, P. F., Hashizume, T., Pomerantz, S. C., McCloskey, J. A., Kawai, G., (1994) A novel modified nucleoside found at the first position of the anticodon of methionine tRNA from bovine liver mitochondria. *Biochemistry* 33, 2234-9.

Murata-Kamiya, N., Kamiya, H., Karino, N., Ueno, Y., Kaji, H., Matsuda, A., Kasai, H. (1999) Formation of 5-formyl-2'-deoxycytidine from 5-methyl-2'-deoxycytidine in duplex DNA by Fenton-type reactions and γ-irradiation. *Nucl. Acids Res.* 27, 4385-4390.

Nichols, R., Andrews, P. C., Zhang, P., Bergstrom, D. E. (1994) A universal nucleoside for use at ambiguous sites in DNA primers *Nature* 369, 492-493.

Ohtsuka, E., Matsuki, S., Ikehara, M., Takahashi, Y. Matsubara, K. (1985) An alternative approach to deoxynucleotides as hybridization probes by insertion of deoxyinosine at ambiguous codon position. *J. Biol. Chem.* 260, 2605-2608.

Pais de Barros, J.-P., Keith, G., El Adlouni, C., Glasser, A.-L., Mack, G., Dirheimer, G., Desgres, J. (1996) 2'-O-Methyl-5-formylcytidine (f5Cm), a new modified nucleotide at the 'wobble' position of two cytoplasmic tRNAsLeu(NAA) from bovine liver. *Nucl. Acids Res.* 24, 1489-96.

Stoss, P., Kaes, E., Eibel, G., Thewalt, U. (1991) Novel pyrimidine and pyrimido[1,2-a]-pyrimidine derivatives. By-products of a guanidine based thymine synthesis. *J. Heterocyclic Chem.* 28, 231-236.

Tanaka, H., Okazaki, T., Tezuka, Y., Hongo, T., Takahashi, Y. (2002) Radical copolymerization of 2-acetoxyacrylates with nitrile monomers and properties of the copolymers. *Polymer,* 43, 1189-1195.

Tomita, K., Ueda, T., Watanabe, K. (1997) 5-Formylcytidine (f5C) found at the wobble position of the anticodon of squid mitochondrial tRNAMetCAU. *Nucleic Acids Symp. Series* 37, 197-198.

Zhang, L., Peritz, A., Meggers, E. (2005) A simple glycol nucleic acid. *J. Am. Chem. Soc.* 127, 4174-4175.

What is claimed is:

1. Compositions of matter are comprise nucleic acids or nucleic acid analogs that carry at least one of the nucleosides described by formula selected from the group consisting of wherein P indicates the site of attachment to the DNA chain, and R is selected from the group consisting of H, OH, O—$CH_3$, and O-allyl.

2. Compositions of matter are comprise nucleic acids or nucleic acid analogs that carry at least one of the nucleosides described by formula selected from the group consisting of wherein P indicates the site of attachment to the DNA chain, and R is selected from the group consisting of H, OH, O—$CH_3$, and O-allyl.

* * * * *